United States Patent [19] [11] Patent Number: 5,945,113
Meinard et al. [45] Date of Patent: Aug. 31, 1999

[54] PESTICIDAL PASTE COMPOSITIONS

[75] Inventors: Colette Meinard; Jean-Claude Suglia, both of Marseilles, France

[73] Assignee: Hoechst Marion Roussel, France

[21] Appl. No.: 08/718,431

[22] PCT Filed: Apr. 12, 1995

[86] PCT No.: PCT/FR95/00471

§ 371 Date: Sep. 24, 1996

§ 102(e) Date: Sep. 24, 1996

[87] PCT Pub. No.: WO95/28082

PCT Pub. Date: Oct. 26, 1995

[30] Foreign Application Priority Data

Apr. 14, 1994 [FR] France .................................. 94 04440

[51] Int. Cl.⁶ .................................................. A01N 25/08
[52] U.S. Cl. .......................... 424/407; 424/406; 424/408; 424/409; 424/421; 424/484; 424/485; 424/486; 424/487; 424/488; 424/44
[58] Field of Search ............................. 424/44, 406–409, 424/421, 484–488

[56] References Cited

U.S. PATENT DOCUMENTS

| | | | |
|---|---|---|---|
| 4,765,984 | 8/1988 | Vellekoop et al. ...................... | 424/441 |
| 5,232,701 | 8/1993 | Ogawa et al. .......................... | 424/408 |
| 5,500,213 | 3/1996 | Roe et al. .............................. | 424/78.37 |
| 5,516,520 | 5/1996 | Yang et al. ............................ | 424/408 |

FOREIGN PATENT DOCUMENTS

| | | |
|---|---|---|
| 55-004336 | 1/1980 | Japan . |
| 62-042902 | 2/1987 | Japan . |
| 5085901 | 4/1993 | Japan . |
| 9201378 | 2/1992 | WIPO . |
| 9217385 | 10/1992 | WIPO . |

OTHER PUBLICATIONS

Pressman in Water Quality/California p. 355 1968.

Websters Dictionary—Paste p. 988.

*Primary Examiner*—Neil S. Levy
*Attorney, Agent, or Firm*—Bierman, Muserlian and Lucas

[57] ABSTRACT

A readily, water-dispersible pesticide formulation in the form of a thick paste containing 1 to 80% by weight of the pesticide, 0.30 to 2.0% by weight of a micropore-generating agent and 30 to 50% by weight of effervescent agents the percentages being based on the total weight of the formulation.

8 Claims, No Drawings

PESTICIDAL PASTE COMPOSITIONS

This application is a 371 of PCT/FR95/00471 filed Apr. 21, 1995

The present invention relates to new pesticide formulations and their preparation process.

A subject of the invention is pesticide formulations being presented in the form of pastes containing:

between 1% and 80% of active ingredient and preferably between 1 and 20% of pure active ingredient or in solution in a solvent, between 0 and 50% of effervescent agents, between 0.30 and 2% of micropore-generating agents.

The formulations of the invention are presented in the form of a thick paste having the property of being effervescent and possessing a microporous structure which gives it very good dispersion in water.

This paste can be presented inside a plastic sachet which is soluble in water, as extruded granules or in blister packs. The last two presentations require a drying operation.

This paste is a composition which possesses a very low viscoelasticity coefficient, it is not a colloidal solution like a gel, but results from an absorption by a solid of a liquid until saturation, the granulometry of the solid particles being comprised between 5 and 40μ.

The active ingredient is in solution in a solvent which is not very volatile and the emulsifying agents contained in this solvent allow the preparation to release the active ingredient in the form of an emulsion after its dilution in water.

The formulations of the invention possess a microporous structure which facilitates their dispersion in water at their time of use. This structure is obtained by bringing about a gaseous release inside the paste when it is prepared. The gas is released by the reaction of the micropore generators and the effervescent agent.

One of the advantages of the invention is to present formulations such as concentrated suspensions or emulsifiable concentrates, which are usually liquid, in the form of a solid or a paste.

Another advantage is to thus avoid any risk of accidental spillage during storage, transportation or handling of the product.

Another advantage is to avoid product losses on the walls of packaging during use.

Another advantage is, in the case where the paste is contained in a water-soluble sachet, to provide a product whose remaining packaging after use contains no trace of active ingredient and whose loss in the case of accidental opening or tearing is nil unlike a liquid or a gel.

The active ingredient is a liquid or solid pesticide, soluble or insoluble in water.

It can be an insecticide, an acaricide, a fungicide or a growth regulator.

As an effervescent agent, a mixture can be used of citric acid and an alkali or alkaline-earth carbonate or hydrogen carbonate, for example sodium or potassium carbonate or calcium carbonate or sodium hydrogen carbonate; acids other than citric acid can be used, for example ascorbic acid or adipic acid.

As a micropore-generating agent, a glycol can be used which reacts slowly with the effervescent agent and causes a carbon dioxide release inside the paste, it is preferably monopropylene glycol.

A more particular subject of the invention is the pesticide formulations containing from 0 to 20% of effervescent agents, or also the formulations containing from 30 to 50% of effervescent agents.

A particular subject of the invention is the formulations containing in addition 3 to 10% of wetting agents or also the formulations containing in addition 20 to 40% of wetting agents.

The wetting agent can be a sodium salt of an aliphatic acid or a lignosulphonate.

A particular subject of the invention is the formulations containing between 5 and 40% of mineral filler or organic filler which can optionally be substituted for the wetting agent.

The mineral fillers must possess a sufficient absorbent power to retain the liquid constituents of the formulation without desorption; they are preferably silicas, for example silica of aerosil or zeosil type or clays such as argirec, vercoryl, or also anhydrous aluminium, potassium or sodium silicates or finally sodium borate.

The organic fillers can be for example chosen from celluloses, starch or corn derivatives, urea, lactose and sugars, polyvinylpyrolidone.

A more particular subject of the invention is the pesticide formulations containing in addition between 0.1 and 0.5% of anti-foam product, 0.01 and 70% of organic solvent, 0.4 and 2% of surfactant, 0.01 and 0.05% of stabilizing agent.

The solvent used is very important for the success of the invention, it has to be a good solvent of the active ingredient, it can be for example an aromatic solvent, such as Solvesso 200® or an isoparaffinic solvent such as Isopar V®.

It can also be a ketone solvent such as isophorone, acetophenone or cyclohexanone combined with different co-solvents such as n-butyl acetate, arcosolv PMA (methoxy propanol acetate), butylbenzoate or also diethylphthalate.

The anti-foam product can be for example Rhodorsil®. The surfactants and the stabilizing agents can be for example those used in the experimental part or also those known to be their equivalents.

A quite particular subject of the invention is the formulations characterized in that the effervescent agent is a mixture of citric acid and sodium carbonate, the formulations characterized in that the micropore-generating agent is a glycol.

Among the preferred formulations of the invention, there can be mentioned quite especially the formulations characterized in that the active ingredient is a fungicide, herbicide or insecticide pesticide and more particularly for the insecticides a pyrethrinoid chosen from the following group of products: deltamethrin, cypermethrin, alphamethrin, tralomethrin, cyhalothrin, fenvalerate, cyfluthrin, flucythrenate, fluvalinate, fenpropathrin, tefluthrin, bifenthrin, acrinathrin, betacyfluthrin, taufluvalinate, lambdacyhalothrin and esfenvalerate.

A quite particular subject of the invention is the formulations in which the pyrethrinoid is deltamethrin, for example those containing from 1 to 15% of deltamethrin.

Also a subject of the invention is a preparation process characterized in that an emulsifiable concentrate containing the active ingredient is prepared, it is poured over the mixture of solid fillers and the whole is mixed to obtain a homogeneous paste.

In a preferred implementation of the process of the invention, the active ingredient is pre-formulated in the form of an emulsifiable concentrate or also in the form of a concentrated suspension in oil.

The formulations according to the invention are introduced into water-soluble sachets, which are then sealed and packed in an outer packaging ensuring the protection of the sachets.

Therefore a subject of the invention is also the formulations as defined above packed in a soluble sachet.

This sachet can be in particular constituted by a multi-layer or single-layer hydrosoluble PVA film or a double-layer laminated film. The NEDI®, EF 300 or EP 300 films can be mentioned for example.

In order to avoid possible swelling during storage of the sachets, between 2 and 10% of dehydrating agent can be added to the composition of the paste such as sodium sulphate, calcium chloride, maleic anhydride or also water-trapping solvents such as cyclohexanone or acetophenone for example.

The formulations thus obtained have a good stability and a good biological activity.

The pastes of the invention diluted in water giving an emulsion are preferably used in agriculture, in the treatment of crops or also in the treatment of animals or in domestic and public hygiene. The areas of use are those of the basic materials used.

The following examples illustrate the invention:

The formulations of the invention are prepared as follows:

A—Preparation of the Basic Emulsifiable Concentrate

The various ingredients, surfactants, solvents, active ingredients, stabilizing agents and others are mixed under agitation until a solution is obtained.

B—Preparation of the Solid Fillers

The solid fillers must have a granulometry of less than 15μ. If this is not the case they will have to be micronized. They are then mixed in a Lödige type machine.

C—Preparation of the Paste

The emulsifiable concentrate is poured over the mixture of solid fillers, the whole is then mixed in a machine until a homogeneous paste is obtained.

D—Preferred Packaging

The paste obtained is placed in a water-soluble sachet, this is then sealed.

Preparation of the Basic Emulsifiable Concentrate

An emulsifiable concentrate was prepared containing:

100% deltamethrin 14.50%

B.H.T. 0.10%

Ca phenylsulphonate 5.03%

Emulsogen EL 360 1.67%

Solvesso 200 78.70%

EXAMPLE 1 a paste was prepared containing 5% of delta-methrin

Anhydrous sodium carbonate 22.5%

Anhydrous citric acid 22.5%

Wetting agent IS powder 20.0%

Monopropyleneglycol 0.4%

Anti-foam agent 425 0.1%

Emulsifiable concentrate of deltamethrin 34.5%

EXAMPLE 2 a paste was prepared corresponding to the formulation

Anhydrous sodium carbonate 12.0%

Anhydrous citric acid 12.0%

Minex 10 32.5%

Morwet D425 2.5%

Wetting agent IS powder 6.0%

Anti-foam agent 425 0.1%

Monopropyleneglycol 0.4%

Emulsifiable concentrate of deltamethrin 34.5%

The pastes of examples 1 and 2 can be packaged in PVA sachets soluble in water. An outer packaging of aluminium coated with PVC can ensure the protection of these sachets.

EXAMPLE 3 granules were prepared with 5% of deltamethrin containing

Anhydrous sodium carbonate 10.0%

Anhydrous citric acid 10.0%

Lactose 1 H20 19.0%

Wetting agent IS powder 26.0%

Anti-foam agent 425 0.1%

Monopropyleneglycol 0.4%

Emulsifiable concentrate of deltamethrin 34.5%

EXAMPLE 4 granules were prepared of formula

Anhydrous sodium carbonate 12.0%

Anhydrous citric acid 12.0%

Minex 10 32.5%

Morwet D425 2.5%

Wetting agent IS powder 6.0%

Anti-foam agent 454 0.1%

Monopropyleneglycol 0.4%

Emulsifiable concentrate of deltamethrin 34.5%

EXAMPLE 5 blister packs or lozenges were prepared with 5% of deltamethrin of formula

Anhydrous sodium carbonate 12.0%

Anhydrous citric acid 12.0%

Minex 10 32.5%

Morwet D425 2.5%

Wetting agent IS powder 4.5%

Monopropyleneglycol 1.9%

Anti-foam agent 425 0.1%

Emulsifiable concentrate of deltamethrin 34.5%

By operating as indicated above, the following formulations were prepared:

The preparations of Examples 6 to 11 are packaged in Nedi EF. 210 film PVA sachets.

| INGREDIENT | Ex. 6 | Ex. 7 | Ex. 8 | Ex. 9 | Ex. 10 | Ex. 11 |
|---|---|---|---|---|---|---|
| DELTA-METHRIN | 5.040 | 5.040 | 5.040 | 5.040 | 5.040 | 5.040 |
| BHT | 0.035 | 0.035 | 0.035 | 0.035 | 0.035 | 0.035 |
| CALCIUM PHENYL-SULPHON-ATE | 0.745 | 0.745 | 0.745 | 0.745 | 0.745 | 0.851 |
| EMULSOGEN EL | 1.738 | 1.738 | 1.738 | 1.738 | 1.738 | 1.631 |
| ISOPHORONE | 21.278 | 21.278 | | 21.278 | 21.278 | 21.278 |
| SOLVESSO 200 | 6.631 | | | | | |
| ARCOSOLV PMA | | 6.631 | | | | |
| ANISOLE | | | 27.909 | | | |
| BUTYL-BENZOATE | | | | 6.631 | | |
| n-BUTYL ACETATE | | | | | 6.631 | |

-continued

| INGREDIENT | Ex. 6 | Ex. 7 | Ex. 8 | Ex. 9 | Ex. 10 | Ex. 11 |
|---|---|---|---|---|---|---|
| DIETHYL-PHTHALATE | | | | | | 6.631 |
| SODIUM CARBONATE | 22.340 | 22.340 | 22.340 | 22.340 | 22.340 | 22.340 |
| CITRIC ACID | 22.340 | 22.340 | 22.340 | 22.340 | 22.340 | 22.340 |
| WETTING AGENT IS | 19.853 | 19.853 | 19.853 | 19.853 | 19.853 | 19.853 |

The preparations of Examples 12 to 17 are packed in Nedi EF AK film PVA sachets.

| INGREDIENT | Ex. 12 | Ex. 13 | Ex. 14 | Ex. 15 | Ex. 16 | Ex. 17 |
|---|---|---|---|---|---|---|
| DELTA-METHRIN | 5.040 | 5.040 | 5.040 | 5.040 | 5.040 | 5.040 |
| BHT | 0.035 | 0.035 | 0.035 | 0.035 | 0.035 | 0.035 |
| CALCIUM PHENYL-SULPHON-ATE | 0.745 | 0.745 | 0.745 | 0.745 | 0.745 | 0.851 |
| EMULSOGEN EL | 1.738 | 1.738 | 1.738 | 1.738 | 1.738 | 1.631 |
| ISOPHORONE | 21.278 | 21.278 | | 21.278 | 21.278 | 21.278 |
| SOLVESSO 200 | 6.631 | | | | | |
| ARCOSOLV PMA | | 6.631 | | | | |
| ANISOLE | | | 27.909 | | | |
| BUTYL-BENZOATE | | | | 6.631 | | |
| n-BUTYL ACETATE | | | | | 6.631 | |
| DIETHYL-PHTHALATE | | | | | | 6.631 |
| SODIUM CARBONATE | 22.340 | 22.340 | 22.340 | 22.340 | 22.340 | 22.340 |
| CITRIC ACID | 22.340 | 22.340 | 22.340 | 22.340 | 22.340 | 22.340 |
| WETTING AGENT IS | 19.853 | 19.853 | 19.853 | 19.853 | 19.853 | 19.853 |

The preparation of Example 18 is packed in Nedi EF.210 film PVA sachets.

The preparation of Example 19 is packed in Nedi EF AK film PVA sachets.

| INGREDIENTS | Ex. 18 Composi. % | Ex. 19 Composi. % |
|---|---|---|
| 98.5% DELTAMETHRIN | 5.04 | 5.04 |
| BHT | 0.10 | 0.10 |
| DIETHYLPHTHALATE | 0.70 | 0.70 |
| ACETOPHENONE | 13.90 | 13.90 |
| EMULSOGEN EL | 1.90 | 1.90 |
| SOLVESSO | 13.76 | 13.76 |
| $Na_2CO_3$ | 15.40 | 15.40 |
| ANHYDROUS CITRIC ACID | 29.30 | 29.30 |
| WETTING AGENT IS | 19.90 | 19.90 |

Preparation of the Basic Emulsifiable Concentrate

An emulsifiable concentrate was prepared containing:

| INGREDIENT | Ex. 20 | Ex. 21 | Ex. 22 | Ex. 23 | Ex. 24 |
|---|---|---|---|---|---|
| 98.5% DELTAMETHRIN | 14.2 | 14.2 | 14.2 | 14.2 | 14.2 |
| BHT | 0.1 | 0.1 | 0.1 | 0.1 | 0.1 |
| CALCIUM PHENYL-SULPHONATE | 3.5 | 3.5 | 3.5 | 3.5 | 3.5 |
| EMULSOGEN EL | 3.5 | 3.5 | 3.5 | 3.5 | 3.5 |
| SOLVESSO 200 | 48.7 | 0 | 0 | 0 | 0 |
| CYCLOHEXANONE | 30.0 | 30.0 | 30.0 | 30.0 | 30.0 |
| ARCOSOLV PMA | | 48.7 | 0 | 0 | 0 |
| ANISOLE | | | 0 | 0 | 0 |
| BUTYLBENZOATE | | | 48.7 | 0 | 0 |
| n-BUTYL ACETATE | | | | 48.7 | 0 |
| DIETHYLPHTHALATE | | | | | 48.7 |

Stability Study

The behaviour during storage of the formulations of the invention was studied.

Biological Study

The insecticide activity of the formulations of the invention was studied on Rhopalosiphum padi (wingless females of the first and second larval stage), the host plant being tea (stage 2 f. Florence-Aurore variety). The formulations of the invention are as effective as the commercial formulation Décis® EC 25 g/l. The formulations therefore have an excellent activity.

We claim:

1. A readily, water-dispersible pesticide formulation consisting essentially of a thick paste containing 1 to 20% by weight of the pesticide, 0.30 to 2.0% by weight of a glycol which releases carbon dioxide in the paste as a micropore-generating agent and 30 to 50% by weight of effervescent agents, the percentages being based on the total weight of the formulation.

2. A formulation of claim 1 also containing 3 to 10% by weight of wetting agents in the paste.

3. A formulation of claim 1 also containing 20 to 40% by weight of wetting agents in the paste.

4. A formulation of claim 1 also containing 5 to 40% by weight of a mineral filler in the paste.

5. A formulation of claim 1 wherein the effervescent agent is a mixture of citric acid and sodium carbonate.

6. A formulation of claim 1 wherein the pesticide is selected from the group consisting of deltamethrin, cypermethrin, alphamethrin, tralomethrin, cyhalothrin, fenvalerate, cyfluthrin, bifenthrin, acrinathrin, betacyfluthrin, taufluvalinate, lambdacyalothrin and esfenvalerate.

7. A formulation of claim 1 wherein the pesticide is deltamethrin.

8. A formulation of claim 7 containing 1 to 15% of deltamethrin.

* * * * *